United States Patent [19]

Holtkamp

[11] Plant 4,532

[45] May 6, 1980

[54] AFRICAN VIOLET PLANT

[75] Inventor: Reinhold Holtkamp, Isselburg, Fed. Rep. of Germany

[73] Assignee: Gessellschaftsvertrag uber die Erfindergemeinschaft "Optimara", Isselburg, Fed. Rep. of Germany

[21] Appl. No.: 2,051

[22] Filed: Jan. 8, 1979

[51] Int. Cl.[2] ..... A01H 5/00

[52] U.S. Cl. ..... Plt./69

[58] Field of Search ..... Plt./69

*Primary Examiner*—Robert E. Bagwill
*Assistant Examiner*—James R. Feyrer
*Attorney, Agent, or Firm*—Donald D. Jeffery

[57] ABSTRACT

An African Violet known by the cultivar name Boston having strong upright stems carrying intensive pink flowers having frilled edges; compact and vigorous growth habit, and leaves which are cupped to form a flat funnel, with the leaves having serrated edges and light-green centers.

1 Drawing Figure

The present invention comprises a new and distinct cultivar of African Violet plant, botanically known as *Saintpaulia ionantha,* and hereinafter referred to by the cultivar name Boston.

The new cultivar, designated during the breeding and selection process as d. 150/1 and 47/78, is a product of a planned breeding program of the present inventor. Boston is principally characterized by its very intensive pink, frilled flowers; compact habit, and leaves which are light green in the center and upturned at the edges to form a generally flat funnel, with the leaf edges being serrated. The light green center characteristic of the leaves is commonly referred to in the industry as a "girl" type cultivar. These traits in combination were not present in previously available commercial cultivars.

The new cultivar was originated from a cross made in a controlled breeding program in Isselburg, Rhineland, Germany. The female, or seed parent was 79 blue, an unpatented "girl" type cultivar. The male, or pollen parent was 17/75, disclosed in U.S. Plant Pat. No. 4,154 and known by the cultivar name Evelyn.

The new cultivar Boston was discovered and selected as a flowering plant within the progeny of the stated cross by me in a controlled environment in Isselburg, Rhineland, Germany.

Asexual reproduction of the new cultivar by leaf cuttings and by division of shoots, as performed by me at Isselburg, Rhineland, Germany, has demonstrated that the combination of characteristics as herein disclosed for the new cultivar are firmly fixed and are retained through successive generations of asexual reproduction.

The following observations, measurements and values describe plants grown in Isselburg, Rhineland, Germany, under greenhouse conditions which closely approximate those generally used in commercial practice.

The following traits have been repeatedly observed and are determined to be basic characteristics of Boston, which in combination distinguish this African Violet as a new and distinct cultivar:

(1) Strong, upright flower stems, with up to 10 flowers on each stem.

(2) Very compact habit (3) Leaves are cupped to generally funnel shaped form with light green centers (4) Leaf edges are serrated (5) The underside of the leaf is reddish-green between the light green veins (6) Very intense pink flower color, with the flowers having frilled eges.

(7) Vigorous growth habit

The accompanying photographic drawing shows a typical specimen plant of the new cultivar. The colors appearing in the photograph are as true as possible with color illustrations of this type.

In the following description, color references are made to the Royal Horticultural Society (RHS) color chart, except for flower color, which is based on the Horticultural Colour Chart, Wilson (HCC), or where general color terms of ordinary significant are used.

Botanical classification: *Saintpaulia ionantha,* Ramat. cv Boston.

Parentage:

*Male parent.*—7/75, disclosed in U.S. Plant Pat. No. 4,154.

*Female parent.*—79 blue, "girl" type.

Propagation: The new cultivar holds its distinguishing characteristics through successive propagations by leaf cuttings and by division of shoots.

Plant: From 9 cm to 10 cm tall when grown in pots, and approximately 20 cm in diameter when fully grown.

Leaves:

*General form.*—Oval-round.

*Diameter.*—55–65 mm.

*Texture.*—Soft-hairy.

*Aspect.*—Sides upturned to form a flat funnel.

*Veins.*—Well pronounced, light green in color.

*Color (upperside).*—147 A.

*Color (underside).*—145 D and 186 C.

*Petiole.*—Red-brownish.

Flowers:

*Buds.*—Ball-shaped, 7–8 mm in diameter.

*Sepals.*—Five, spear-shaped.

*Color.*—Brown-reddish.

*Calyx.*—Basifixed.

*Aspect.*—Funnel-shaped.

*Peduncle.*—Dark brown-reddish.

Individual Flowers:

*Size.*—48 mm in total flower diameter.

*Color (upperside).*—629/1, (HCC).

*Color (underside).*—Slightly lighter than 629/1 (HCC).

*Borne.*—Up to 9 flowers per stem.

*Shape.*—Five petals; two small, three large.

*Corolla.*—All petals are frilled, the two small petals being 19 mm long and 19 mm wide and the three large petals being 24 mm long and 23 mm wide.

Arrangement: The plant has 8–10 flower stems, each stem carrying up to 9 flowers.

Flowering time: 6–7 weeks after potting, the first flowers appear; 3 weeks later the plant is in full flower.

Reproductive organs:

*Stamens.*—Two.

*Anthers.*—Four, color 7-B.

*Arrangements.*—Basifixed.

*Filaments.*—Flat-oval, yellow-green to light pink in color.

*Styles.*—Pink

*Pollen color.*—7-C

*Roots.*—Young roots are white; when older turning brownish.

*Disease resistance.*—Good.

General Observations: Boston is a compact vigorous grower. The leaves are round to oval and flat funnel-shaped with light green centers. The edges are serrated and slightly waved, and thicker than normal for violet leaves. The flower stems are very strong and straight. The petiole has on the upperside toward the leaf a groove and is reddish-brown in color. The flowers have frilled edges and intensive pink color.

I claim:

1. A new and distinct cultivar of African Violet, as described and illustrated, known by the cultivar name Boston and characterized by the combined features of strong upright stems carrying intensive pink flowers having frilled edges; compact and vigorous growth habit, and by its leaves which are cupped to form a flat funnel, with the leaves having serrated edges and light green centers.

* * * * *

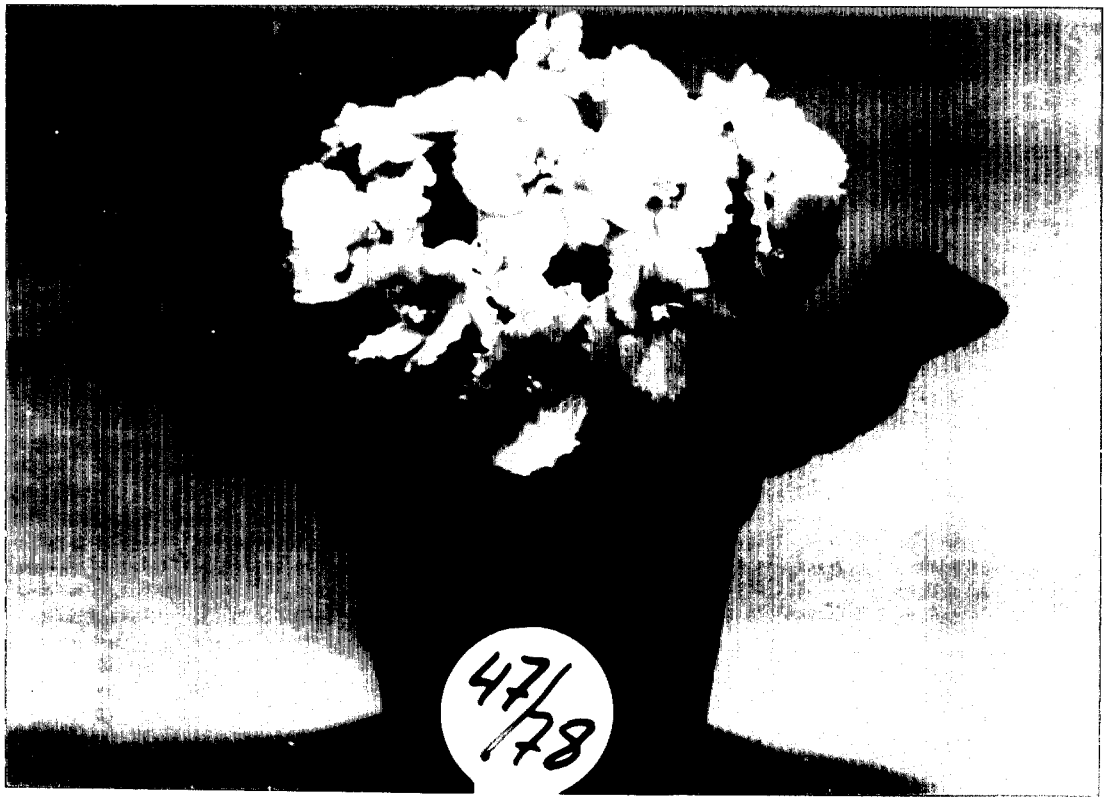
47/78